United States Patent [19]

Kuban et al.

[11] Patent Number: 5,313,306

[45] Date of Patent: May 17, 1994

[54] OMNIVIEW MOTIONLESS CAMERA ENDOSCOPY SYSTEM

[75] Inventors: Daniel P. Kuban, Oak Ridge; H. Lee Martin; Steven D. Zimmermann, both of Knoxville, all of Tenn.

[73] Assignee: TeleRobotics International, Inc., Knoxville, Tenn.

[21] Appl. No.: 68,776

[22] Filed: Jun. 1, 1993

Related U.S. Application Data

[63] Continuation-in-part of Ser. No. 14,508, Feb. 8, 1993, which is a continuation-in-part of Ser. No. 699,366, May 13, 1991, Pat. No. 5,185,667.

[51] Int. Cl.$^5$ .............................................. H04N 5/30
[52] U.S. Cl. ........................................ 348/65; 382/44; 348/39; 348/240
[58] Field of Search ............... 358/209, 225, 98, 108, 358/87, 85, 903, 229, 180, 160; 382/44; 395/137–139; H04N 5/30

[56] References Cited

U.S. PATENT DOCUMENTS

| 4,661,855 | 4/1987 | Gülek | 358/225 |
|---|---|---|---|
| 4,728,839 | 3/1988 | Coughlan et al. | |
| 4,772,942 | 9/1988 | Tuck | |
| 4,858,002 | 8/1989 | Zobel | 358/225 |
| 4,918,473 | 4/1990 | Blackshear | |
| 4,945,367 | 7/1990 | Blackshear | |
| 5,023,725 | 6/1991 | McCutchen | |
| 5,067,019 | 11/1991 | Juday et al. | |
| 5,068,735 | 11/1991 | Tuchiya et al. | |
| 5,185,667 | 2/1993 | Zimmermann | |
| 5,231,673 | 7/1993 | Elenga | 382/44 |

Primary Examiner—James J. Groody
Assistant Examiner—Glenton B. Burgess
Attorney, Agent, or Firm—Pitts & Brittian

[57] ABSTRACT

A endoscopic-type device for omnidirectional image viewing providing electronic pan-and-tilt orientation, rotation, and magnification within a selected field-of-view for use in applications in various environments such as in internal medicine inspection, monitoring, and surgery. The imaging device (using optical or infrared images) is based on the effect that the image from a wide angle lens, which produces a circular image of an entire field-of-view, can be mathematically corrected using high speed electronic circuitry. More specifically, an incoming image from a endoscope image acquisition source, including a wide angle lens, is transmitted through an image conduit and captured by a camera that produces output signals according to that image. A transformation of these output signals is performed for the viewing region of interest and viewing direction, and a corrected image is output as a video image signal for viewing, recording, or analysis. Multiple simultaneous images can be output from a single input image.

19 Claims, 5 Drawing Sheets

OMNIVIEW MOTIONLESS CAMERA ENDOSCOPY SYSTEM

This is a continuation-in-part patent application based upon patent application Ser. No. 08/014,508 filed Feb. 8, 1993 which is a continuation-in-part patent application based upon parent application Ser. No. 07/699,366 filed on May 13, 1991, now U.S. Pat. No. 5,185,667 issued Feb. 9, 1993.

TECHNICAL FIELD

The present invention relates to an apparatus, algorithm, and method for transforming single perspective-distorted field-of-view images into single or multiple non-distorted, normal perspective images at any orientation, rotation, and magnification within the field-of-view, and for using the resultant system for endoscopic applications. The viewing direction, orientation, and magnification are controlled by various input means. More particularly, this apparatus is the electronic equivalent of a mechanical pan, tilt, zoom, and rotation camera viewing system with no moving mechanisms, and is typically utilized for internal medical imaging or industrial inspection in combination with a video camera attached to an endoscope, laparoscope, cystoscope, thoroscope or other fiberscope or borescope device.

BACKGROUND ART

Camera viewing systems are utilized in abundance for surveillance, inspection, security, internal medicine and remote sensing. Remote viewing is critical, for example, for robotic manipulation tasks. Close viewing is necessary for detailed manipulation tasks while wide-angle viewing aids positioning of the robotic system to avoid collisions with the work space. The majority of these systems use either a fixed-mount camera with a limited viewing field to reduce distortion, utilize mechanical pan-and-tilt platforms and mechanized zoom lenses to orient the camera and magnify its image, or attach a camera to a rigid or flexible glass bundle that conveys an image from inside the human body to the camera located exterior the body. In the applications where orientation of the camera and magnification of its image are required, the mechanical solution is large in size and can subtend a significant volume making the viewing system difficult to conceal or use internally. Several cameras are usually necessary to provide wide-angle viewing of the work space.

Camera viewing systems that use internal optics to provide wide viewing angles have also been developed in order to minimize the size and volume of the camera and the intrusion into the viewing area. These systems rely on the movement of either a mirror or prism to change the tilt-angle of orientation, and provide mechanical rotation of the entire camera to change the pan angle of orientation. Additional lenses are used to minimize distortion.

Using this means, the size of the camera orientation system can be minimized, but "blind spots" in the center of the view result. Also, these systems typically have no means of magnifying or rotating the image and or producing multiple images from a single camera.

References that may be relevant to the evaluation of the present invention are U.S. Pat. No. 4,772,942 issued to M. J. Tuck on Sep. 20, 1988; U.S. Pat. No. 5,023,725 issued to D. McCutchen on Jun. 11, 1991; U.S. Pat. No. 5,067,019 issued to R. D. Juday on Nov. 19, 1991; and U.S. Pat. No. 5,068,735 issued to K. Tuchiya, et al on Nov. 26, 1991.

Accordingly, it is an object of the present invention to provide an apparatus that can provide an image of any portion of the viewing space within a selected field-of-view without moving the apparatus, and then electronically correct for visual distortions of the view.

It is another object of the present invention to provide horizontal orientation (pan), vertical orientation (tilt) and rotational orientation (rotation) of the viewing direction with no moving mechanisms.

It is another object of the present invention to provide the ability to magnify or scale any portion of the image (zoom in and out) electronically.

It is another object of the present invention to provide electronic control of image enhancing operations such as the image intensity (iris level), filtering, detection, sharpening, etc.

It is another object of the present invention to be able to accomplish pan, tilt, zoom, rotation, and iris adjustments with simple inputs made by a lay person from a joystick, keyboard controller, or computer controlled means.

It is also an object of the present invention to provide accurate control of the absolute viewing direction and orientations using said input devices.

A further object of the present invention is to provide the ability to produce multiple images with different orientations and magnifications simultaneously from a single input image to one or more output monitors.

Another object of the present invention is to be able to provide these images at real-time video rates, e.g. thirty transformed images per second, and to support various display format standards such as the National Television Standards Committee RS-170 signal format and/or higher resolution formats currently under development.

It is also an object of the present invention to provide a system that can be used for observation of internal organs and body portions, with optical views of these environments corrected electronically to remove distortion so as to facilitate this observation. This can be during diagnosis, treatment, surgery and the like.

It is also an object of the present invention to provide an enhanced system that can be used for inspection of industrial equipment in extremely confined spaces such as engines, turbines, pipes, valves, etc.

These and other objects of the present invention will become apparent upon consideration of the drawings hereinafter in combination with a complete description thereof.

DISCLOSURE OF THE INVENTION

In accordance with the present invention, there is provided an omnidirectional viewing system that produces the equivalent of pan, tilt, zoom, and rotation within a selected field-of-view with no moving parts. Further, the present invention includes means for controlling this omnidirectional viewing in applications such as endoscopy. This device includes a means for digitizing an incoming or prerecorded video image signal, transforming a portion of the video image based upon operator or preselected commands, and producing one or more output images that are in correct perspective for human viewing. In one embodiment, the incoming image is produced by a fisheye lens which has a wide angle field-of-view. A portion of the captured image, either in real time or as prerecorded, containing a region-of-interest is transformed into a perspective correct image by an image processing computer. The image processing computer provides direct mapping of the image region-of-interest into a corrected image using an orthogonal set of transformation algorithms. The viewing orientation is designated by a command signal generated by either a human operator or computerized input. The transformed image is deposited in a second electronic memory buffer where it is then manipulated to produce the output image or images as requested by the command signal.

BEST MODE FOR CARRYING OUT THE INVENTION

In order to minimize the size of the camera orientation system while maintaining the ability to zoom, a camera orientation system that utilizes electronic image transformations rather than mechanisms was developed. While numerous patents on mechanical pan-and-tilt systems have been filed, no approach using strictly electronic transforms and wide angle optics is known to have been successfully implemented other than the afore-cited U.S. Pat. No. 5,185,667. In addition, the electro-optical approach utilized in the present invention allows multiple unique images to be extracted from the output of a single camera. As utilized herein, the term "endoscopy" has a wide range including, but not limited to, devices that convey an image from one location to another via a glass tube, fiber bundle, etc, to be received by a camera and then transmitted in an electrical form. The term "wide angle" as used herein means a field-of-view of about eighty degrees or greater. Motivation for this device came from viewing system requirements in internal medical applications and confined industrial inspection applications where the operating envelop of the equipment is a significant constraint to task accomplishment.

Figure 1:
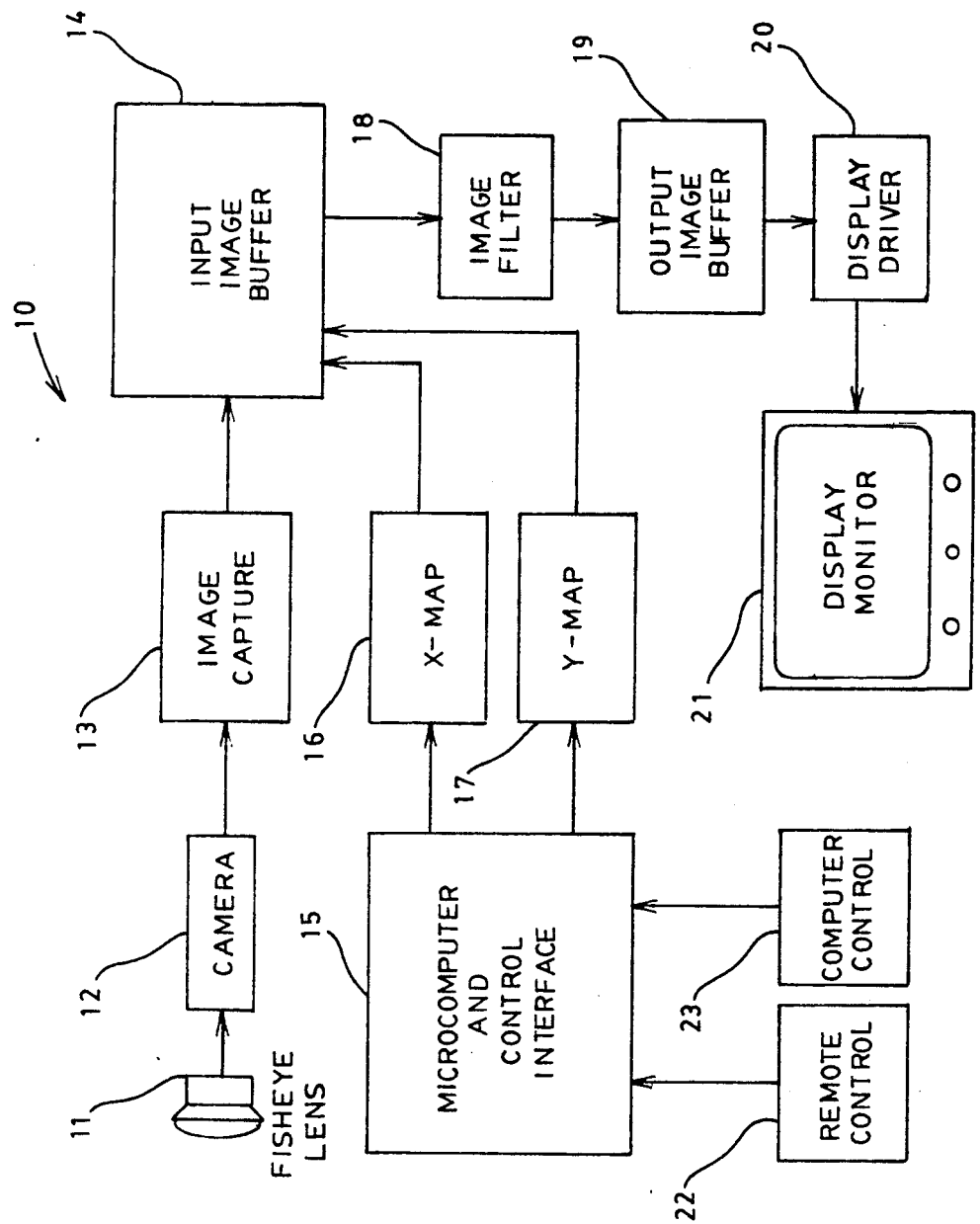
FIG. 1 shows a schematic block diagram of the signal processing portion of the present invention illustrating the major components thereof.

The principles of the optical transform utilized in the present invention can be understood by reference to the prior art system 10 of FIG. 1. (This is also set forth in the afore-cited U.S. Pat. No. 5,185,667 that is incorporated herein by reference.) Shown schematically at 11 is a wide angle, e.g., a fisheye, lens that provides an image of the environment with up to a one-hundred eighty degree field-of-view. The lens is attached to a camera 12 which converts the optical image into an electrical signal. These signals are then digitized electronically 13 and stored in an image buffer 14 within the present invention. An image processing system consisting of an X-MAP and a Y-MAP processor shown as 16 and 17, respectively, performs the two-dimensional transform mapping. The image transform processors are controlled by the microcomputer and control interface 15. The microcomputer control interface provides initialization and transform parameter calculation for the system. The control interface also determines the desired transformation coefficients based on orientation angle, magnification, rotation, and light sensitivity input from an input means such as a joystick controller 22 or computer input means 23. The transformed image is filtered by a 2-dimensional convolution filter 18 and the output of the filtered image is stored in an output image buffer 19. The output image buffer 19 is scanned out by display electronics 20 to a video display device 21 for viewing.

A range of lens types can be accommodated to support various fields of view. The lens optics 11 correspond directly with the mathematical coefficients used with the X-MAP and Y-MAP processors 16 and 17 to transform the image. The capability to pan and tilt the output image remains even though a different maximum field of view is provided with a different lens element.

The system can be realized by proper combination of a number of optical and electronic devices. The lens 11 is exemplified by any of a series of wide angle endoscopes from, for example, Olympus. Any video source 12 and image capturing device 13 that converts the optical image into electronic memory can serve as the input for the invention. Input and output image buffers 14 and 19 can be constructed using Texas Instrument TMS44C251 video random access memory chips or their equivalents. The control interface can be accomplished with any of a number of microcontrollers including the Intel 80C196. The X-MAP and Y-MAP transform processors 16 and 17 and image filtering 19 can be accomplished with application specific integrated circuits or other means as will be known to persons skilled in the art. The display driver can also be accomplished with integrated circuits such as the Texas Instruments TMS34061. The output video signal can be of the NTSC RS-170, for example, compatible with most commercial television displays in the United States. Remote control 22 and computer control 23 are accomplished via readily available switches and/or computer systems that also will be well known. These components function as a system to select a portion of the input image (fisheye or other wide angle) and then mathematically transform the image to provide the proper prospective for output. The keys to the success of the invention include:

(1) the entire input image need not be transformed, only the portion of interest;

(2) the required mathematical transform is predictable based on the lens characteristics; and (3) calibration coefficients can be modified by the end user to correct for any endoscope/camera combination supporting all available endoscope systems.

Figure 3:
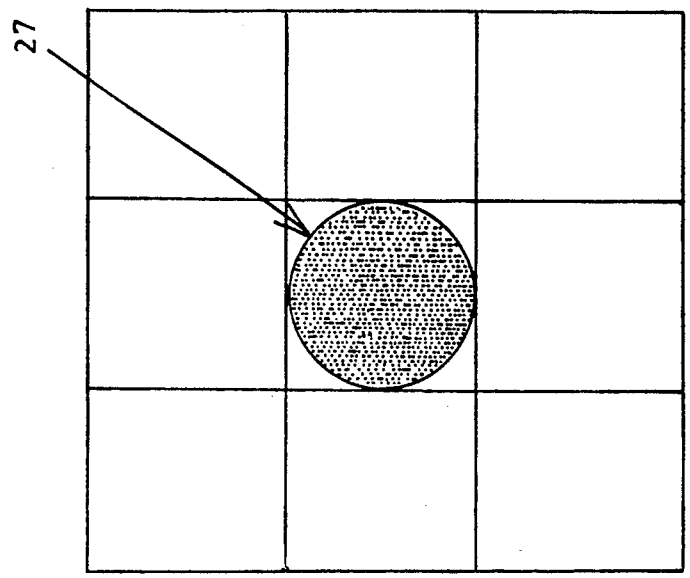
FIG. 3 is an exemplary drawing of the output image after correction for a desired image orientation and magnification within the original image.
Figure 2:
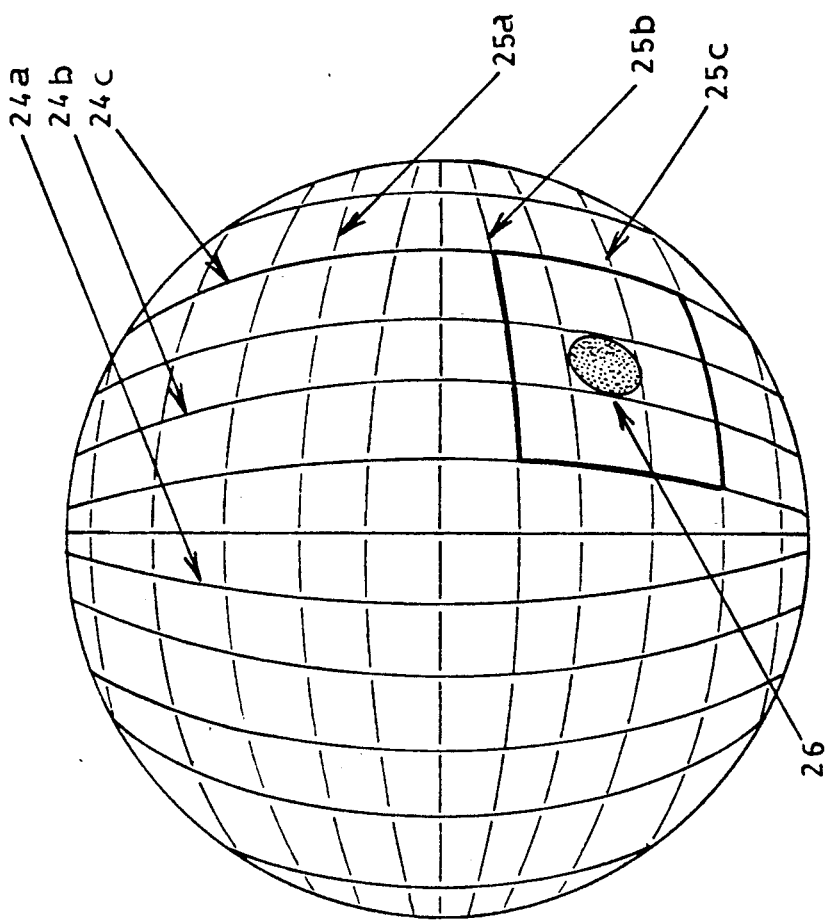
FIG. 2 is an exemplary drawing of a typical fisheye image used as input by the present invention. Lenses having other field-of-view values will produce images with similar distortion, particularly when the field-of-view is about eighty degrees or greater.

The transformation that occurs between the input memory buffer 14 and the output memory buffer 19, as controlled by the two coordinated transformation circuits 16 and 17, is better understood by referring to FIGS. 2 and 3. The image shown in FIG. 2 is a rendering of the image of a grid pattern produced by a fisheye lens. This image has a field-of-view of 180 degrees and shows the contents of the environment throughout an entire hemisphere. Notice that the resulting image in FIG. 2 is significantly distorted relative to human perception. Similar distortion will be obtained even with lesser field-of-view lenses. Vertical grid lines in the environment appear in the image plane as 24a, 24b, and 24c. Horizontal grid lines in the environment appear in the image plane as 25a, 25b, and 25c. The image of an object is exemplified by 26. A portion of the image in FIG. 2 has been corrected, magnified, and rotated to produce the image shown in FIG. 3. Item 27 shows the corrected representation of the object in the output display. The results shown in the image in FIG. 3 can be produced from any portion of the image of FIG. 2 using the present invention. The corrected perspective of the view is demonstrated by the straightening of the grid pattern displayed in FIG. 3. In the present invention, these transformations can be performed at real-time video rates (e.g., thirty times per second), compatible with commercial video standards.

The transformation portion of the invention as described has the capability to pan and tilt the output image through the entire field of view of the lens element by changing the input means, e.g. the joystick or computer, to the controller. This allows a large area to be scanned for information as can be useful in many applications, such as in internal medicine and confined industrial inspection. The image can also be rotated through any portion of 360 degrees on its axis changing the perceived vertical of the displayed image. This capability provides the ability to align the vertical image with the operator's perspective to maintain a proper perspective in the image display regardless of the pan or tilt angle of the image. The invention also supports modifications in the magnification used to display the output image. This is commensurate with a zoom function that allows a change in the field of view of the output image. This function is extremely useful for surgical (inspection, surgery, etc.) operations. The magnitude of zoom provided is a function of the resolution of the input camera, the resolution of the output display, and the amount of picture element (pixel) averaging that is used in a given display. The invention supports all of these functions to provide capabilities associated with traditional mechanical pan (through 180 degrees), tilt (through 180 degrees), rotation (through 360 degrees), and zoom devices. The digital system also supports image intensity scaling that emulates the functionality of a mechanical iris by shifting the intensity of the displayed image based on commands from the user or an external computer.

The postulates and equations that follow are based on the image transformation portion of the present invention utilizing a wide angle lens as the optical element. These also apply to other field-of-view lens systems. There are two basic properties and two basic postulates that describe the perfect wide angle lens system. The first property of such a lens is that the lens has a $2\pi$ steradian field-of-view and the image it produces is a circle. The second property is that all objects in the field-of-view are in focus, i.e. the perfect wide angle lens has an infinite depth-of-field. The two important postulates of this lens system (refer to FIGS. 4 and 5) are stated as follows:

Postulate 1: Azimuth angle invariability —For object points that lie in a content plane that is perpendicular to the image plane and passes through the image plane origin, all such points are mapped as image points onto the line of intersection between the image plane and the content plane, i.e. along a radial line. The azimuth angle of the image points is therefore invariant to elevation and object distance changes within the content plane.

Postulate 2: Equidistant Projection Rule —The radial distance, r, from the image plane origin along the azimuth angle containing the projection of the object point is linearly proportional to the zenith angle $\beta$, where $\beta$ is defined as the angle between a perpendicular line through the image plane origin and the line from the image plane origin to the object point. Thus the relationship:

$$r = k\beta \qquad (1)$$

Figure 4:
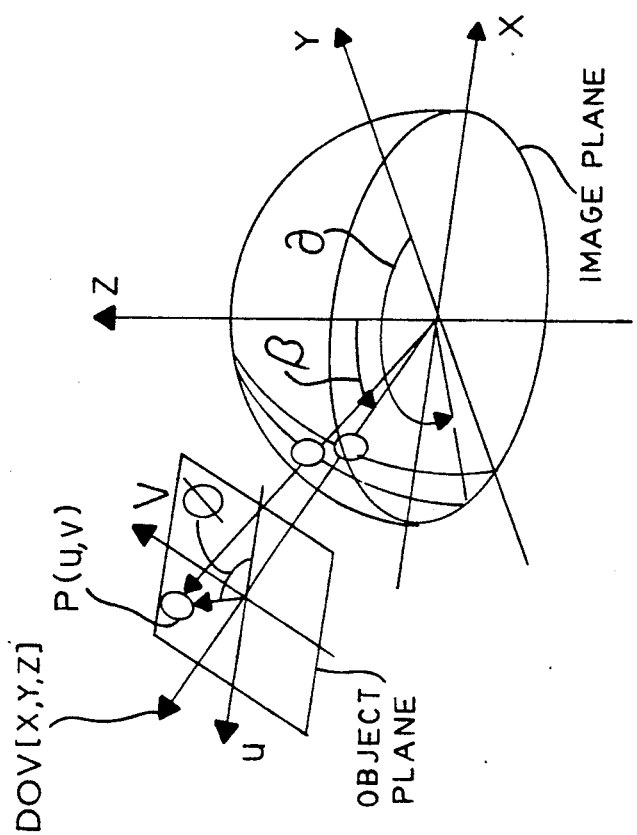
FIG. 4 is a schematic diagram of the fundamental geometry that the present invention embodies to accomplish the image transformation.

Using these properties and postulates as the foundation of the lens system, the mathematical transformation for obtaining a perspective corrected image can be determined. FIG. 4 shows the coordinate reference frames for the object plane and the image plane. The coordinates u,v describe object points within the object plane. The coordinates x,y,z describe points within the image coordinate frame of reference.

The object plane shown in FIG. 4 is a typical region of interest to determine the mapping relationship onto the image plane to properly correct the object. The direction of view vector, DOV[x,y,z], determines the zenith and azimuth angles for mapping the object plane, UV, onto the image plane, XY. The object plane is defined to be perpendicular to the vector, DOV[x,y,z].

The location of the origin of the object plane in terms of the image plane [x,y,z] in spherical coordinates is given by:

$$x = D \sin \beta \cos \partial$$

$$y = D \sin \beta \sin \partial$$

$$z = D \cos \beta \qquad (2)$$

where D=scaler length from the image plane origin to the object plane origin, $\beta$ is the zenith angle, and $\partial$ is the azimuth angle in image plane spherical coordinates. The origin of object plane is represented as a vector using the components given in Equation 1 as:

$$DOV[x,y,z] = [D \sin \beta \cos \partial, D \sin \beta \sin \partial, D \cos \beta] \qquad (3)$$

DOV[x,y,z] is perpendicular to the object plane and its scaler magnitude D provides the distance to the object plane. By aligning the YZ plane with the direction of action of DOV[x,y,z], the azimuth angle $\partial$ becomes either 90 degrees or 270 degrees and therefore the x component becomes zero resulting in the DOV[x,y,z] coordinates:

$$DOV[x,y,z] = 0, -D \sin \beta, D \cos\beta \qquad (4)$$

Figure 5:
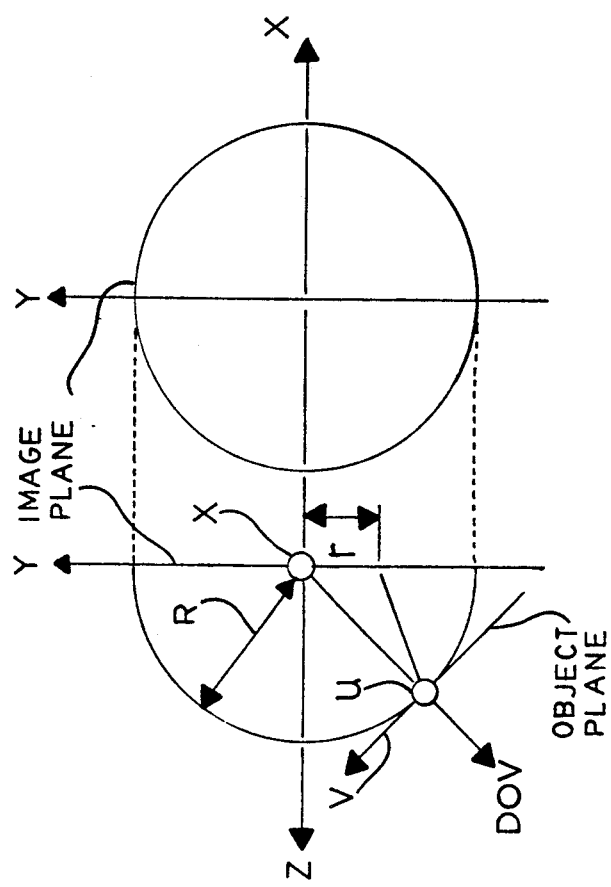
FIG. 5 is a schematic diagram demonstrating the projection of the object plane and position vector into image plane coordinates.

Referring now to FIG. 5, the object point relative to the UV plane origin in coordinates relative to the origin of the image plane is given by the following:

$$x = u$$

$$y = v \cos \beta$$

$$z = v \sin \beta \quad (5)$$

therefore, the coordinates of a point P(u,v) that lies in the object plane can be represented as a vector P[x,y,z] in image plane coordinates:

$$P[x,y,z] = [u, v \cos \beta, v \sin \beta] \quad (6)$$

where P[x,y,z] describes the position of the object point in image coordinates relative to the origin of the UV plane. The object vector o[x,y,z] that describes the object point in image coordinates is then given by:

$$O[x,y,z] = DOV[x,y,z] + P[x,y,z] \quad (7)$$

$$O[x,y,z] = [u, v \cos \beta - D \sin \beta, v \sin \beta + D \cos \beta] \quad (8)$$

Projection onto a hemisphere of radius R attached to the image plane is determined by scaling the object vector O[x,y,z] to produce a surface vector s[x,y,z]:

$$S[x,y,z] = \frac{RO[x,y,z]}{|O[x,y,z]|} \quad (9)$$

By substituting for the components of O[x,y,z] from Equation 8, the vector S[x,y,z] describing the image point mapping onto the hemisphere becomes:

$$S[x,y,z] = \frac{RO[u, (v\cos\beta - D\sin\beta), (v\sin\beta + D\cos\beta)]}{\sqrt{u^2 + (v\cos\beta - D\sin\beta)^2 + (v\sin\beta + D\cos\beta)^2}} \quad (10)$$

The denominator in Equation 10 represents the length or absolute value of the vector O[x,y,z] and can be simplified through algebraic and trigonometric manipulation to give:

$$S[x,y,z] = \frac{RO[u, (v\cos\beta - D\sin\beta), (v\sin\beta + D\cos\beta)]}{\sqrt{u^2 + v^2 + D^2}} \quad (11)$$

From Equation 11, the mapping onto the two-dimensional image plane can be obtained for both x and y as:

$$x = \frac{Ru}{\sqrt{u^2 + v^2 + D^2}} \quad (12)$$

$$y = \frac{R(v\cos\beta - D\sin\beta)}{\sqrt{u^2 + v^2 + D^2}} \quad (13)$$

Additionally, the image plane center to object plane distance D can be represented in terms of the image circular radius R by the relation:

$$D = mR \quad (14)$$

where m represents the scale factor in radial units R from the image plane origin to the object plane origin. Substituting Equation into Equations 12 and 13 provides a means for obtaining an effective scaling operation or magnification which can be used to provide zoom operation.

$$x = \frac{Ru}{\sqrt{u^2 + v^2 + m^2R^2}} \quad (15)$$

$$y = \frac{R(v\cos\beta - mR\sin\beta)}{\sqrt{u^2 + v^2 + m^2R^2}} \quad (16)$$

Using the equations for two-dimensional rotation of axes for both the UV object plane and the XY image plane the last two equations can be further manipulated to provide a more general set of equations that provides for rotation within the image plane and rotation within the object plane.

$$x = \frac{R[uA - vB + mR\sin\beta\sin\partial]}{\sqrt{u^2 + v^2 + m^2R^2}} \quad (17)$$

$$y = \frac{R[uC - vD - mR\sin\beta\cos\partial]}{\sqrt{u^2 + v^2 + m^2R^2}} \quad (18)$$

where:

$$A = (\cos \phi \cos \partial - \sin \phi \sin \partial \cos \beta)$$

$$B = (\sin \phi \cos \partial + \cos \phi \sin \partial \cos \beta)$$

$$C = (\cos \phi \sin \partial + \sin \phi \cos \partial \cos \beta)$$

$$D = (\sin \phi \sin \partial - \cos \phi \cos \partial \cos \beta) \quad (19)$$

and where:
R = radius of the image circle
$\beta$ = zenith angle
$\partial$ = Azimuth angle in image plane
$\phi$ = Object plane rotation angle
m = Magnification
u,v = object plane coordinates
x,y = image plane coordinates The Equations 17 and 18 provide a direct mapping from the UV space to the XY image space and are the fundamental mathematical result that supports the functioning of the present omnidirectional viewing system with no moving parts. By knowing the desired zenith, azimuth, and object plane rotation angles and the magnification, the locations of x and y in the imaging array can be determined. This approach provides a means to transform an image from the input video buffer to the output video buffer exactly. Also, the image system is completely symmetrical about the zenith, therefore, the vector assignments and resulting signs of various components can be chosen differently depending on the desired orientation of the object plane with respect to the image plane. In addition, these postulates and mathematical equations can be modified for various lens elements as necessary for the desired field-of-view coverage in a given application.

The input means defines the zenith angle, $\beta$, the azimuth angle, $\partial$, the object rotation, $\phi$, and the magnification, m. These values are substituted into Equations 19 to determine values for substitution into Equations 17 and 18. The image circle radius, R, is a fixed value that is determined by the camera lens and element relationship. The variables u and v vary throughout the object plane determining the values for x and y in the image plane coordinates.

From the foregoing, it can be seen that a wide angle lens provides a substantially hemispherical view that is captured by a camera. The image is then transformed into a corrected image at a desired pan, tilt, magnification, rotation, and focus based on the desired view as described by a control input. The image is then output to a television display with the perspective corrected. Accordingly, no mechanical devices are required to attain this extensive analysis and presentation of the view of an environment through 180 degrees of pan, 180 degrees of tilt, 360 degrees of rotation, and various degrees of zoom magnification.

Figure 6:
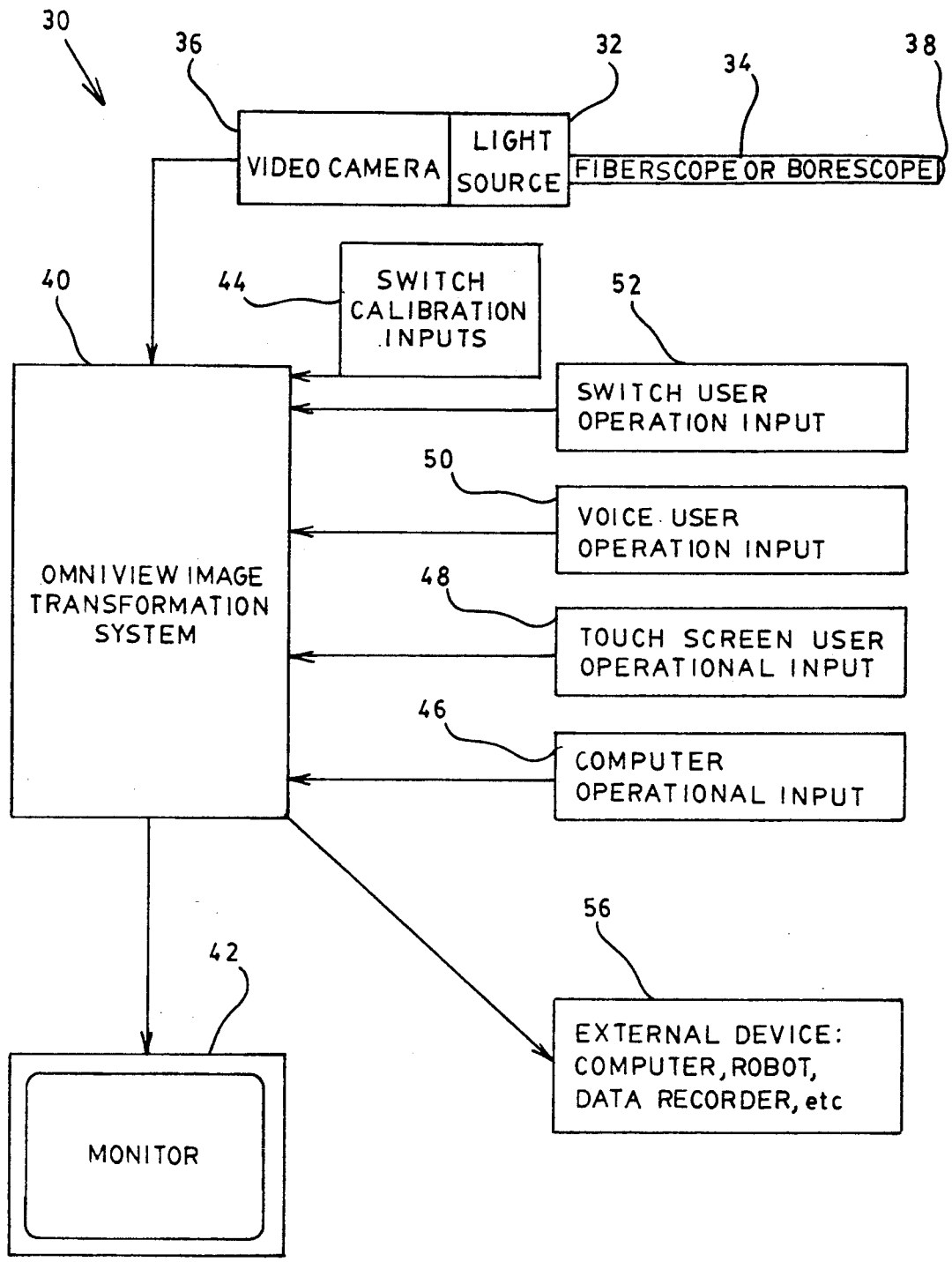
FIG. 6 is a block diagram of the present invention as utilized for applications such as internal medical endoscopy incorporating the basic transformation of video images obtained with, for example, wide angle lenses to correct for optical distortions due to the lenses, together with the control of the view parameters and display configuration.
Figure 7:
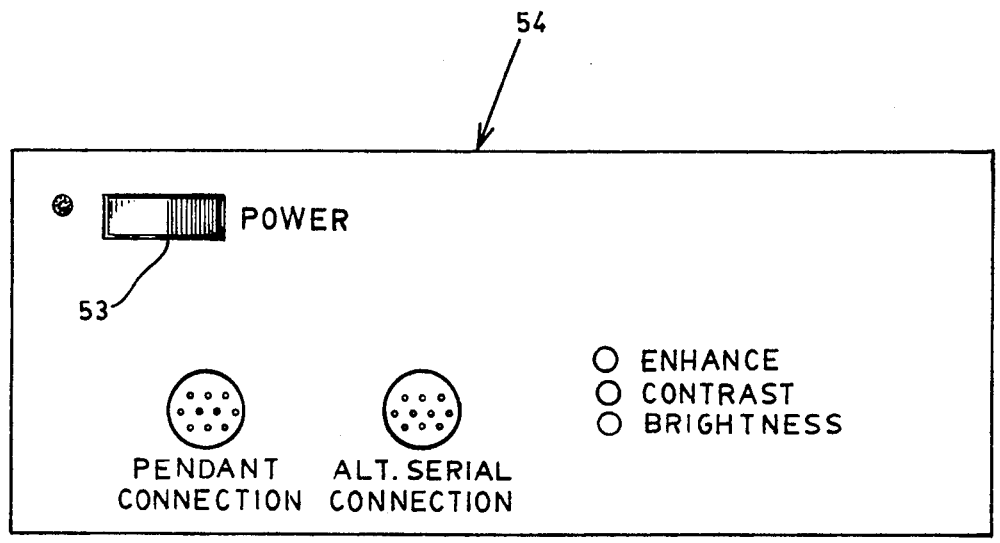
FIG. 7 shows one typical operator interface embodiment of the present device.

As indicated above, one application for the perspective correction of images obtained with a motionless wide angle camera is in the field of endoscopy. The term "endoscopy" is meant to include internal medicine inspection and surgical operations as well. It is often desired to continuously or periodically view a selected environment to determine activity in that environment. The term "environment" is meant to include such areas as a patient's thorax (chest), gastrointestinal (stomach), orthopedic areas (joints), colon, etc. This activity might be, for example, grasping or cutting of some object relative to that environment. It might also be evaluating some infection that has taken place in that environment. It may be desired to carry out this endoscopy upon demand by an operator. An endoscopy system according to one embodiment of the present invention is indicated generally at 30 of FIG. 6. Typically, an endoscope is comprised of a light source 32 and an image conduit 34. This image conduit 34, which can be flexible or solid, directs light to a patient or machine and brings an image from within the patient or machine. In this embodiment this image is directed into an imaging head of the camera 36 located outside the patient or machine. Positioned at the distal end of the image conduit 34 is a wide angle lens 38. The output from the camera 36 is an electrical signal related to the elements of an image as seen by the camera. These signals are directly presented to an image transformation system 40 for enhancement and display to a monitor 42, such as a television screen. Any of the known resolutions, or resolutions of anticipated technology, can be utilized in this presentation. Various external elements are utilized to control the operation of the transformation system 40. For example, one set of discrete switches 44 are used for the selection of calibration parameters including image center Y, image center X, image radius, contrast and brightness. Other embodiments provide for an input to be accomplished with a computer input 46, a touch screen 48 or a voice input 50. FIG. 7 illustrates a typical front panel 54 for this device. This panel includes switch 53 which powers the device.

A second set of discrete switches 52 is mounted on a remote keypad that can be sterilized for use in a sterile environment.

Figure 8:
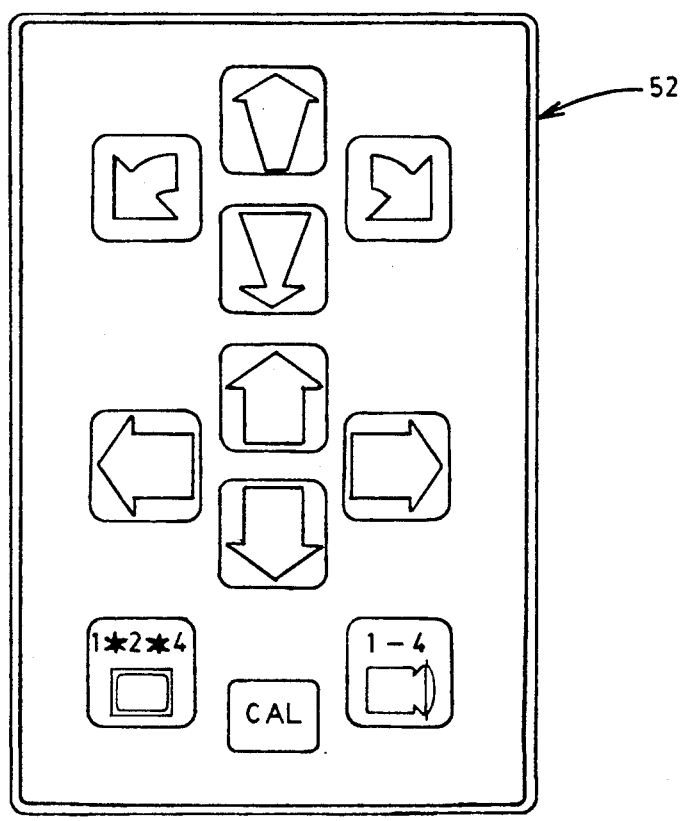
FIG. 8 illustrates an embodiment of a pendant keypad configuration for the present endoscopy system.

FIG. 8 shows an example of the keypad configuration for the present embodiment of the invention. This set of switches 52 provides for active control of the pan angle, tilt angle, magnifications, rotation, display configuration, and activation of the camera 32 by the user. Of course, the functions indicated therein could be performed equally well with an analog joystick input or discrete switch input.

Referring again to FIG. 6, the system is capable of providing output angular information on the display 42. Alternatively, or in combination, the output information can be transferred to an external device 56. This external device can be a computer, a data recorder, an actuating device such as a robot or the like that can be useful in locating specific viewed items relative to the location of the endoscope, etc. Such information could be utilized by these external devices to automatically position "tools" to cut, lase or extract material from the field of view when a stereoscopic system is used and a simple triangulation is implemented between two systems.

The present invention has significant importance in the field of internal medicine and confined industrial inspection. The distal end of the image conduit carrying the lens can be inserted to a point of interest by a user of the device. Without any motion of this distal end, the user can view any one area, or a group of areas, within the field of view. Through the introduction of an appropriate angular correction, etc., the user can obtain an enhanced view (or views) with a proper perspective. This allows for the movement of other devices in the region of the end of the endoscope such that various medical procedures can be accomplished quickly and effectively.

From the foregoing, it will be understood by those versed in the art that an advanced endoscopy system has been provided. This system utilizes an endoscope for placement within the environment to be viewed, this endoscope having a wide angle lens at a distal end in the environment. A video camera is used to produce electrical signals corresponding to the image as seen by the lens. The perspective of images obtained with the lens/camera are corrected through transformation according to the technology of U.S. Pat. No. 5,185,667 directly. Many operational conditions are selectable including image tilt, pan, zoom and rotation. Further, multi-image displays can be obtained, and the images can be incrementally scanned. The system provides for automatic operation coupled with user operation if desired.

While certain specific elements of construction are indicated throughout the description of the present invention, these are given for illustration and not for limitation. Thus, the invention is to be limited only by the appended claims and their equivalents.

We claim:

1. A device for providing perspective and distortion corrected views, in a desired format, of a selected portion of a field of view in an environment, said device comprising:

an imaging system for receiving selected optical and infrared images of said selected portion of a field of view and for producing output signals corresponding to said selected optical and infrared images, said imaging system including a light source, an image conduit to conduct light from said light source into the environment and return said images from the environment, and a video camera to create said output signals;

a lens attached to a distal end of said image conduit of said imaging system, said distal end for placement in the environment, for conveyance of said selected optical and infrared images through said image conduit of said imaging system;

image capture circuitry for receiving and providing digitized signals from said output signals from said imaging system;

image transform circuitry for processing said digitized signals from said image capture circuitry according to selected viewing angles of pan, tilt, and rotation and percentage of magnification, and for producing output signals according to a combination of said digitized signals and said selected viewing angles of pan, tilt, and rotation and percentage of magnification;

an input for selected user and external computer input to select said angles of pan, tilt, and rotation and percentage of magnification, and for converting said selected viewing angles of pan, tilt, and rotation and percentage of magnification for input to said image transform circuitry to control said processing of said image transform circuitry; and an output connected to said image transform circuitry for recording said perspective and distortion corrected views according to said selected viewing angles of pan, tilt, and rotation and percentage of magnification.

2. An endoscopy device for providing perspective corrected views of a selected portion of perspective distorted optical images from an environment into a desired format, said device comprising:

an imaging system for receiving optical images from the environment and for producing output signals corresponding to said perspective distorted optical images, said imaging system including light source, an image conduit for conveying light from said light source into the environment, a wide angle lens at a distal end of said image conduit in the environment for optical conveyance of said optical images through said image conduit and a video camera positioned exterior the environment to receive images from said lens, said optical images to said video camera being perspective distorted by said wide angle lens;

image capture circuitry for receiving, and producing digitized signals from, said output signals from said imaging system;

image transform circuitry for processing said digitized signals from said image capture circuitry according to selected viewing angles of pan, tilt, and rotation and percentage of magnification for producing output signals of perspective corrected images according to a combination of said digitized signals and said selected viewing angles of pan, tilt, and rotation and percentage of magnification;

an input for selecting said viewing angles of pan, tilt, and rotation and percentage of magnification, and for producing signals to control said processing of said image transform circuitry as to said viewing angles of pan, tilt, and rotation and percentage of magnification; and an output connected to said image transform circuitry for recording said perspective corrected views according to said selected viewing angles of pan, tilt, and rotation and percentage of magnification.

3. The device of claim 2 wherein said imaging system further comprises a video recorder for receiving and recording said output signals of said video camera for selective input to said image transform circuitry.

4. The device of claim 2 further comprising a further input for inputting control signals to said image transform circuitry to achieve simultaneous multiple perspective corrected views in said output and selected scanning of said perspective corrected views in said output.

5. The device of claim 4 wherein said input and said further input have selective user inputs including computer keyboard input, voice activated input and touch screen input.

6. The device of claim 4 wherein said further input includes discrete switches to control said processing of said image transform circuitry, said discrete switches in a keypad, said keypad being sterilizable when said device is utilized for medical purposes.

7. The device of claim 1 wherein said image transform circuitry is programmed to implement the following two equations:

$$x = \frac{R[uA - vB + mR\sin\beta\sin\partial]}{\sqrt{u^2 + v^2 + m^2R^2}}$$

$$y = \frac{R[uC - vD - mR\sin\beta\cos\partial]}{\sqrt{u^2 + v^2 + m^2R^2}}$$

where:
$A = (\cos\phi \cos\partial - \sin\phi \sin\partial \cos\beta)$
$B = (\sin\phi \cos\partial + \cos\phi \sin\partial \cos\beta)$
$C = (\cos\phi \sin\partial + \sin\phi \cos\partial \cos\beta)$
$D = (\sin\phi \sin\partial - \cos\phi \cos\partial \cos\beta)$
and where:
R = radius of the image circle
$\beta$ = zenith angle
$\partial$ = Azimuth angle in image plane
$\phi$ = Object plane rotation angle
m = Magnification
u,v = object plane coordinates
x,y = image plane coordinates.

8. The device of claim 2 wherein said image transform circuitry is programmed to implement the following two equations:

$$x = \frac{R[uA - vB + mR\sin\beta\sin\partial]}{\sqrt{u^2 + v^2 + m^2R^2}}$$

$$y = \frac{R[uC - vD - mR\sin\beta\cos\partial]}{\sqrt{u^2 + v^2 + m^2R^2}}$$

where:
$A = (\cos\phi \cos\partial - \sin\phi \sin\partial \cos\beta)$
$B = (\sin\phi \cos\partial + \cos\phi \sin\partial \cos\beta)$
$C = (\cos\phi \sin\partial + \sin\phi \cos\partial \cos\beta)$
$D = (\sin\phi \sin\partial - \cos\phi \cos\partial \cos\beta)$
and where:
R = radius of the image circle
$\beta$ = zenith angle
$\partial$ = Azimuth angle in image plane
$\phi$ = Object plane rotation angle
m = Magnification
u,v = object plane coordinates
x,y = image plane coordinates.

9. An endoscopic device for use in internal medicine to provide perspective corrected views of a selected portion of perspective distorted optical images from an environment within a patient into a desired format, said device comprising:

an imaging system for receiving optical images from the environment and for producing output signals corresponding to said perspective distorted optical images, said imaging system including an image conduit, a video camera at a proximal end of said image conduit exterior the environment, a wide angle lens at a distal end of said image conduit for placement within the environment for optical conveyance of said optical images from the environment through said image conduit to said video camera, said optical images to said video camera being perspective distorted by said wide angle lens, said imaging system being sterilizable;

image transform circuitry for processing said output signals from said imaging system according to selected viewing angles of pan, tilt, and rotation and percentage of magnification for producing output signals of perspective corrected images according to a combination of said digitized signals and said selected viewing angles of pan, tilt, and rotation and percentage of magnification;

an input for selecting said viewing angles of pan, tilt, and rotation and percentage of magnification, and for producing signals to control said processing of said image transform circuitry as to said viewing angles of pan, tilt, and rotation and percentage of magnification; and a further input for inputting control signals to said image transform circuitry to achieve multiple perspective corrected views in said output means and selected scanning of said video camera; and an output connected to said image transform circuitry for recording said perspective corrected views according to said selected viewing angles of pan, tilt, and rotation and percentage of magnification;

wherein said image transform circuitry is programmed to implement the following two equations:

$$x = \frac{R[uA - vB + mR\sin\beta\sin\partial]}{\sqrt{u^2 + v^2 + m^2R^2}}$$

$$y = \frac{R[uC - vD - mR\sin\beta\cos\partial]}{\sqrt{u^2 + v^2 + m^2R^2}}$$

where:
A = (cos $\phi$ cos $\partial$ − sin $\phi$ sin $\partial$ cos $\beta$)
B = (sin $\phi$ cos $\partial$ + cos $\phi$ sin $\partial$ cos $\beta$)
C = (cos $\phi$ sin $\partial$ + sin $\phi$ cos $\partial$ cos $\beta$)
D = (sin $\phi$ sin $\partial$ − cos $\phi$ cos $\partial$ cos $\beta$)
and where:
R = radius of the image circle
$\beta$ = zenith angle
$\partial$ = Azimuth angle in image plane
$\phi$ = Object plane rotation angle
m = Magnification
u,v = object plane coordinates
x,y = image plane coordinates.

10. The device of claim 9 wherein said input and said further input have selective user inputs including computer keyboard input, voice activated input and touch screen input.

11. The device of claim 10 wherein said further input includes discrete switches to control said processing of said image transform circuitry, said discrete switches in a keypad, said keypad being sterilizable.

12. The device of claim 10 wherein said further input comprises discrete switches to input said selected angles of pan, tilt, and rotation and percentage of magnification into said image transform circuitry.

13. The device of claim 11 further comprising an output line from said image transform circuitry to selectively activate actuating equipment within the environment.

14. The device of claim 9 wherein said imaging system further comprises a light source to direct light through said image conduit into said environment within the patient.

15. An endoscopic device for use in confined industrial inspection to provide perspective corrected views of a selected portion of perspective distorted optical images from an environment within an industrial device into a desired format, said device comprising:

an imaging system for receiving optical images from the environment and for producing output signals corresponding to said perspective distorted optical images, said imaging system including an image conduit, a video camera at a proximal end of said image conduit exterior the environment, a wide angle lens at a distal end of said image conduit for placement within the environment for optical conveyance of said optical images from the environment through said image conduit to said video camera, said optical images to said video camera being perspective distorted by said wide angle lens;

image transform circuitry for processing said output signals from said imaging system according to selected viewing angles of pan, tilt, and rotation and percentage of magnification for producing output signals of perspective corrected images according to a combination of said digitized signals and said selected viewing angles of pan, tilt, and rotation and percentage of magnification;

an input for selecting said viewing angles of pan, tilt, and rotation and percentage of magnification, and for producing signals to control said processing of said image transform circuitry as to said viewing angles of pan, tilt, and rotation and percentage of magnification; and a further input for inputting control signals to said image transform circuitry to achieve multiple perspective corrected views in said output means and selected scanning of said video camera; and an output connected to said image transform circuitry for recording said perspective corrected views according to said selected viewing angles of pan, tilt, and rotation and percentage of magnification;

wherein said image transform circuitry is programmed to implement the following two equations:

$$x = \frac{R[uA - vB + mR\sin\beta\sin\partial]}{\sqrt{u^2 + v^2 + m^2R^2}}$$

$$y = \frac{R[uC - vD - mR\sin\beta\cos\partial]}{\sqrt{u^2 + v^2 + m^2R^2}}$$

where:
A = (cos $\phi$ cos $\partial$ − sin $\phi$ sin $\partial$ cos $\beta$)
B = (sin $\phi$ cos $\partial$ + cos $\phi$ sin $\partial$ cos $\beta$)
C = (cos $\phi$ sin $\partial$ + cos $\phi$ cos $\partial$ cos $\beta$)
D = (sin $\phi$ sin $\partial$ − cos $\phi$ cos $\partial$ cos $\beta$)
and where:
R = radius of the image circle
$\beta$ = zenith angle
$\partial$ = Azimuth angle in image plane
$\phi$ = Object plane rotation angle
m = Magnification
u,v = object plane coordinates
x,y = image plane coordinates.

16. The device of claim 15 wherein said further input includes discrete switches to control said processing of said image transform circuitry, said discrete switches enclosed in a keypad.

17. The device of claim 15 wherein said further input comprises discrete switches to input said selected angles of pan, tilt, and rotation and percentage of magnification into said image transform circuitry.

18. The device of claim 16 further comprising an output line from said image transform circuitry to selectively activate actuating equipment within the environment.

19. The device of claim 15 wherein said imaging system further comprises a light source to direct light through said image conduit into the environment within the industrial device.

* * * * *